United States Patent
Al-Ali et al.

(10) Patent No.: US 11,484,231 B2
(45) Date of Patent: *Nov. 1, 2022

(54) REPROCESSING OF A PHYSIOLOGICAL SENSOR

(71) Applicant: Masimo Corporation, Irvine, CA (US)

(72) Inventors: Ammar Al-Ali, San Juan Capistrano, CA (US); Yassir Abdul-Hafiz, Irvine, CA (US); Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/911,781

(22) Filed: Jun. 25, 2020

(65) Prior Publication Data
US 2020/0323472 A1 Oct. 15, 2020

Related U.S. Application Data

(63) Continuation of application No. 15/592,945, filed on May 11, 2017, now Pat. No. 10,729,362, which is a (Continued)

(51) Int. Cl.
*A61B 5/1455* (2006.01)
*G01R 3/00* (2006.01)
(Continued)

(52) U.S. Cl.
CPC ........ *A61B 5/14552* (2013.01); *A61B 5/0205* (2013.01); *A61B 5/1495* (2013.01); (Continued)

(58) Field of Classification Search
CPC .............. A61B 5/1455; A61B 5/14551; A61B 5/14552; A61B 5/68; A61B 5/6801; (Continued)

(56) References Cited

U.S. PATENT DOCUMENTS 4,960,128 A  10/1990  Gordon et al.
4,964,408 A  10/1990  Hink et al.
(Continued)

FOREIGN PATENT DOCUMENTS

EP  0 850 594  7/1998
EP  2 544 591  1/2013

OTHER PUBLICATIONS

US 9,579,050 B2, 02/2017, Al-Ali (withdrawn)
(Continued)

*Primary Examiner* — Eric F Winakur
(74) *Attorney, Agent, or Firm* — Knobbe, Martens, Olson & Bear, LLP

(57) ABSTRACT

Because reprocessing or refurbishing of physiological sensors reuses large portions of an existing sensor, the material costs for refurbishing sensors is significantly lower than the material costs for making an entirely new sensor. Typically, existing reprocessors replace only the adhesive portion of an adhesive physiological sensor and reuse the sensing components. However, re-using the sensing components can reduce the reliability of the refurbished sensor and/or reduce the number of sensors eligible for refurbishing due to out-of-specification sensor components. It is therefore desirable to provide a process for refurbishing physiological sensors that replaces the sensing components of the sensor. While sensing components are replaced, generally, sensor cable and/or patient monitor attachments are retained, resulting in cost savings over producing new sensors.

17 Claims, 10 Drawing Sheets

Related U.S. Application Data continuation of application No. 14/078,843, filed on Nov. 13, 2013, now Pat. No. 9,662,052, which is a continuation of application No. 13/041,803, filed on Mar. 7, 2011, now Pat. No. 8,584,345.

(60) Provisional application No. 61/311,668, filed on Mar. 8, 2010.

(51) Int. Cl.
  *A61B 5/1495* (2006.01)
  *B23P 6/00* (2006.01)
  *A61B 5/0205* (2006.01)

(52) U.S. Cl.
  CPC .......... *B23P 6/00* (2013.01); *A61B 2560/0276* (2013.01); *Y10T 29/49002* (2015.01); *Y10T 29/4902* (2015.01); *Y10T 29/49004* (2015.01); *Y10T 29/49007* (2015.01)

(58) Field of Classification Search
  CPC ........... A61B 2562/22; Y10T 29/49004; Y10T 29/49007; Y10T 29/4902
  See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,104,846 A | 8/2000 | Hodgson et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |

(56) References Cited

U.S. PATENT DOCUMENTS

| | | |
|---|---|---|
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,676,600 B1 | 1/2004 | Conero et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,153,709 B1 | 12/2006 | Purdy et al. |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,300,630 B2 | 11/2007 | Cronin et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |

(56) References Cited

U.S. PATENT DOCUMENTS

| | | |
|---|---|---|
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,696,468 B2 | 4/2010 | Lohmann |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,152,441 B2 | 4/2012 | Hofmann |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |

(56) References Cited

U.S. PATENT DOCUMENTS

| | | |
|---|---|---|
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |

(56) References Cited

U.S. PATENT DOCUMENTS

| | | |
|---|---|---|
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,729,362 B2 | 8/2020 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0004403 A1 | 1/2003 | Drinan et al. |
| 2003/0013975 A1 | 1/2003 | Kiani |
| 2003/0018243 A1 | 1/2003 | Gerhardt et al. |
| 2003/0135099 A1 | 7/2003 | Al-Ali |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0101848 A1 | 5/2005 | Al-Ali et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0177771 A1 | 8/2007 | Tanaka et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0088467 A1 | 4/2008 | Al-Ali |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al Ali et al. |
| 2012/0046557 A1 | 2/2012 | Kiani |

(56) References Cited

U.S. PATENT DOCUMENTS

| | | |
|---|---|---|
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |

(56) References Cited

U.S. PATENT DOCUMENTS

| | | |
|---|---|---|
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |

OTHER PUBLICATIONS

EP Office Action dated Jul. 28, 2015 for Application No. 11709258.5 in 5 pages.

EP Office Action dated Jan. 16, 2018 for Application No. 11709258.5 in 4 pages.

EP Office Action dated Jan. 3, 2019 for Application No. 11709258.5 in 5 pages.

International Preliminary Report on Patentability for International Application No. PCT/US2011/027444 dated Sep. 20, 2012.

International Search Report and Written Opinion for International Application No. PCT/US2011/027444 dated Jun. 28, 2011.

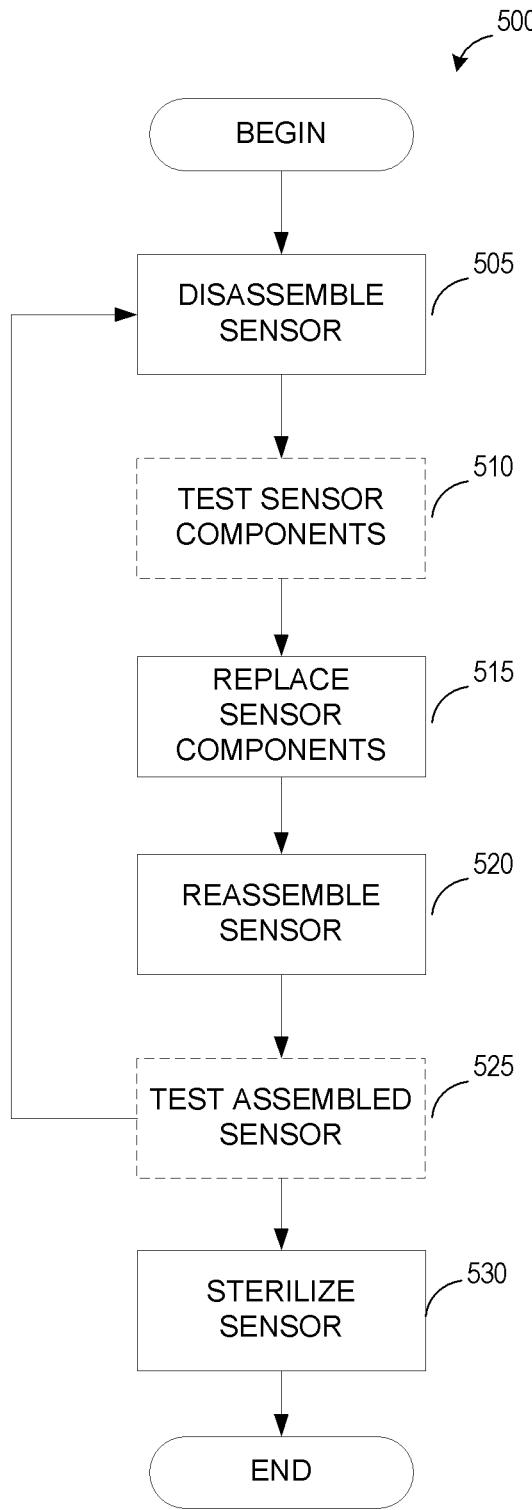 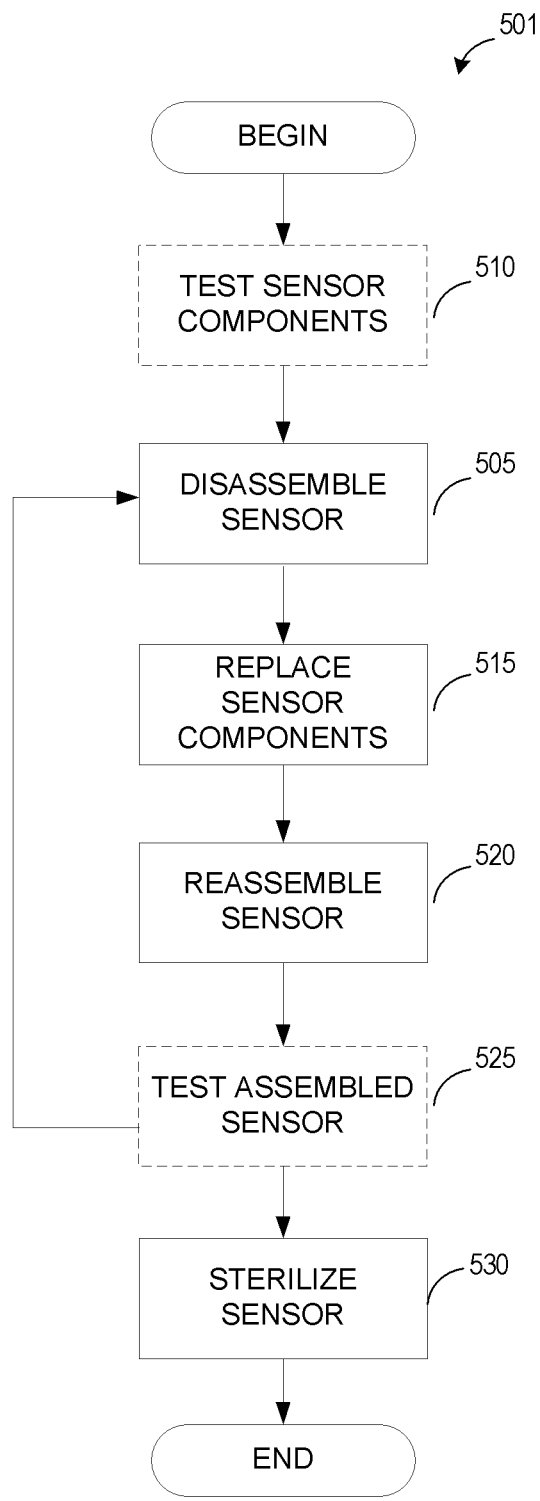
*FIG. 5A*  *FIG. 5B*

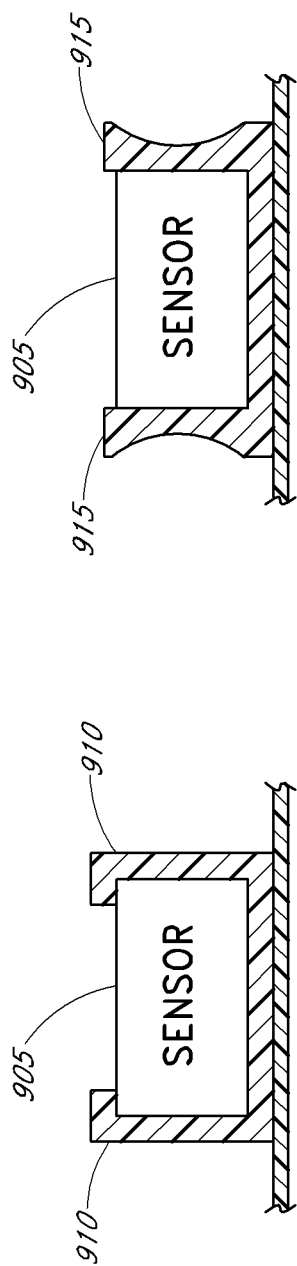

REPROCESSING OF A PHYSIOLOGICAL SENSOR

CROSS-REFERENCE TO RELATED APPLICATIONS

This application is a continuation of U.S. patent application Ser. No. 15/592,945, filed May 11, 2017, titled "REPROCESSING OF A PHYSIOLOGICAL SENSOR," which application is a continuation of U.S. patent application Ser. No. 14/078,843, filed Nov. 13, 2013, titled "REPROCESSING OF A PHYSIOLOGICAL SENSOR," which application is a continuation of U.S. patent application Ser. No. 13/041,803, filed Mar. 7, 2011, titled "REPROCESSING OF A PHYSIOLOGICAL SENSOR," which claims the benefit of priority under 35 U.S.C. § 119(e) of U.S. Provisional Application No. 61/311,668, filed Mar. 8, 2010, titled "REPROCESSING OF A PHYSIOLOGICAL SENSOR." Each of the above identified applications is hereby incorporated by reference in its entirety herein.

FIELD OF THE DISCLOSURE

The present disclosure relates to medical sensors and specifically to reprocessing or refurbishing of medical sensors.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to SpO2, such as HbCO, HbMet and/or Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp.

In order reduce costs, some hospitals or medical institutions choose to purchase refurbished or reprocessed sensors. Typically, these sensors are single-use sensors and are meant to be used by a single patient. Refurbishers receive used sensors, usually from the hospitals, and replace adhesive portions of the sensor while keeping the sensing components unchanged. However, such re-use of the sensing components can decrease reliability of the readings of the sensors as the sensing components of the sensor suffer from wear, damage, misalignment, or the like due to use.

Typically, for adhesive physiological sensors, reprocessors simply replace the adhesive tape on the sensors without replacing additional components. This could potentially lead to sensors with degraded sensing performance. On the other hand, if the reprocessor institutes strict functional testing procedures, sensors can be disposed of even if a large portion of a sensor, other than the sensing component, is still within specification.

SUMMARY OF THE DISCLOSURE

Because reprocessing or refurbishing of physiological sensors reuses large portions of an existing sensor, the material costs for refurbishing sensors is significantly lower than the material costs for making an entirely new sensor. Typically, existing reprocessors replace only the adhesive portion of an adhesive physiological sensor and reuse the sensing components. However, re-using the sensing components can reduce the reliability of the refurbished sensor and/or reduce the number of sensors eligible for refurbishing due to out-of-specification sensor components. It is therefore desirable to provide a process for refurbishing physiological sensors that replaces the sensing components of the sensor. While sensing components are replaced, generally, sensor cable and/or patient monitor attachments are retained, resulting in cost savings over producing new sensors.

BRIEF DESCRIPTION OF THE DRAWINGS

FIGS. 5A and 5B illustrate flow charts for embodiments of a refurbishing process for replacing sensor components;

FIGS. 9A and 9B illustrate embodiments of mechanical sensor component holders.

DETAILED DESCRIPTION

Reprocessing includes operations performed to render a used reusable or single-use device patient-ready or to allow an unused product that has been opened to be patient-ready. Reprocessing can be done in-house or by a third-party reprocessor. Whether reprocessesing is done in-house or through a third party, reprocessing generally involves cleaning, sterilization, function testing and/or replacement of components.

In this context, cleaning can mean removal of visible contaminants and environmental debris (including microscopic particles of tissue, body waste, body fluids, dirt, and/or dust). Function testing verifies that a device will perform as intended. Sterilization in the context of reprocessing can mean meeting domestic and/or international sterilization standards, such as meeting a sterility assurance level of 10–6 (i.e. a theoretical one in a million chance that an organism could survive).

Figure 1A:
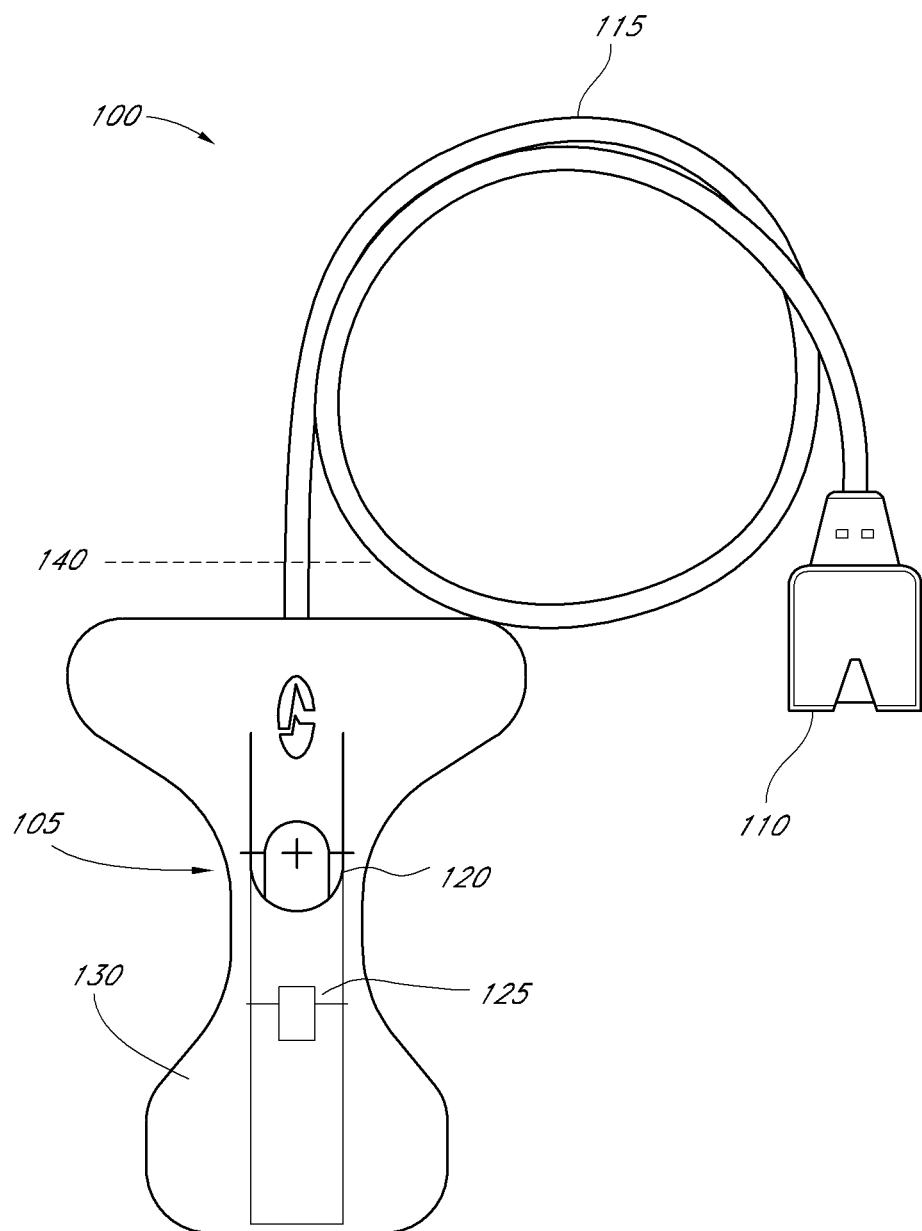
FIG. 1A illustrates an example non-invasive physiological sensor which can be used with a sensor refurbishing process according to embodiments of the disclosure.

FIG. 1A illustrates a top view of an example non-invasive physiological sensor 100 which can be used with a sensor refurbishing process according to embodiments of the disclosure. In certain embodiments, the sensor 100 may allow for the measurement of blood constituents and related parameters, including oxygen saturation, HbCO, HBMet and/or pulse rate. The sensor 100 may advantageously be a non-invasive optical sensor capable of emitting light and outputting one or more signals indicative of attenuation of that light by body tissue. For example, the sensor 100 may be a pulse oximeter sensor including, for example, a red emitter, an infrared emitter, and a photodiode detector. The sensor 100 may be attached to a patient's finger, earlobe, or foot. For a finger, the sensor can be configured so that the emitters project light from one side of the finger, through the outer tissue of the finger, and into the blood vessels and capillaries contained inside. The photodiode can be positioned at the opposite side of the finger to detect the emitted light as it emerges from the outer tissues of the finger. The photodiode can generate a signal based on the emitted light and relay that signal to the sensor 100. The sensor 100 can determine blood oxygen saturation by, for example, computing the differential absorption by the arterial blood of the two or more wavelengths emitted by the sensor.

In certain embodiments, the sensor 100 can be adapted to attach to a tissue site. The sensor 100 can include a sensor assembly 105, a patient monitor connector 110, a sensor cable 115 operatively connecting the sensor assembly 105 and a monitor connector 110. The monitor connector 110 can be adapted to connect to a patient monitor which may include a display providing readouts of measured parameters, such as oxygen saturation, pulse rate, HbCO and/or HbMet to name a few. The sensor assembly 105 can comprise one or more emitters 120 and a detector 125. In certain embodiments, the sensor 100 utilizes an adhesive attachment mechanism 130, such as an adhesive layer, for attaching the sensor 100 to a tissue site. In some embodiments, the sensor can be disposable, re-usable, or partially re-usable and partially disposable.

After the sensor 100 is used on a patient, the used sensor can be refurbished through a refurbishing process. Typically, refurbishing or reprocessing of medical sensors can include disassembling sensors into sub-components, testing sensor components, replacing sensor components, reassembly of the components, testing of the sensor and/or sterilization of the sensor. In some embodiments of the reprocessing process, the entire sensor assembly 105 can be replaced, reusing only the cable 115 and monitor connector 110. In certain embodiments, the cable 115 and/or monitor connector 110 can also be replaced. In some embodiments, only portions of the sensor assembly 105, such as the sensing components, 120, 125 are replaced.

In some embodiments, the whole sensor assembly 105 is replaced. Replacing the whole sensor assembly 105 can reduce or eliminate the need to disassemble the sensor and/or test components during the refurbishing process. For example, the replacement sensor can be pre-tested and/or calibrated beforehand, such as during production, so that testing the sensor components is not required. During reprocessing, the old sensor assembly 105 can be detached from the cable 115, for example, by cutting along a section of the cable 140. The cable 115 can be cut along any section, but preferably is cut near the sensor assembly 105 so that a larger portion of the cable 115 can be reused. After the old sensor assembly 105 is removed, a new sensor assembly is attached to the old cable and tested to determine whether the sensor 100 operates correctly.

In some embodiments, the new sensor assembly includes a cable portion, typically of short length, for attachment to a reprocessed cable. In some embodiments, the cable portion can terminate in a connector for simplified attachment to the reprocessed cable.

Figure 1B:
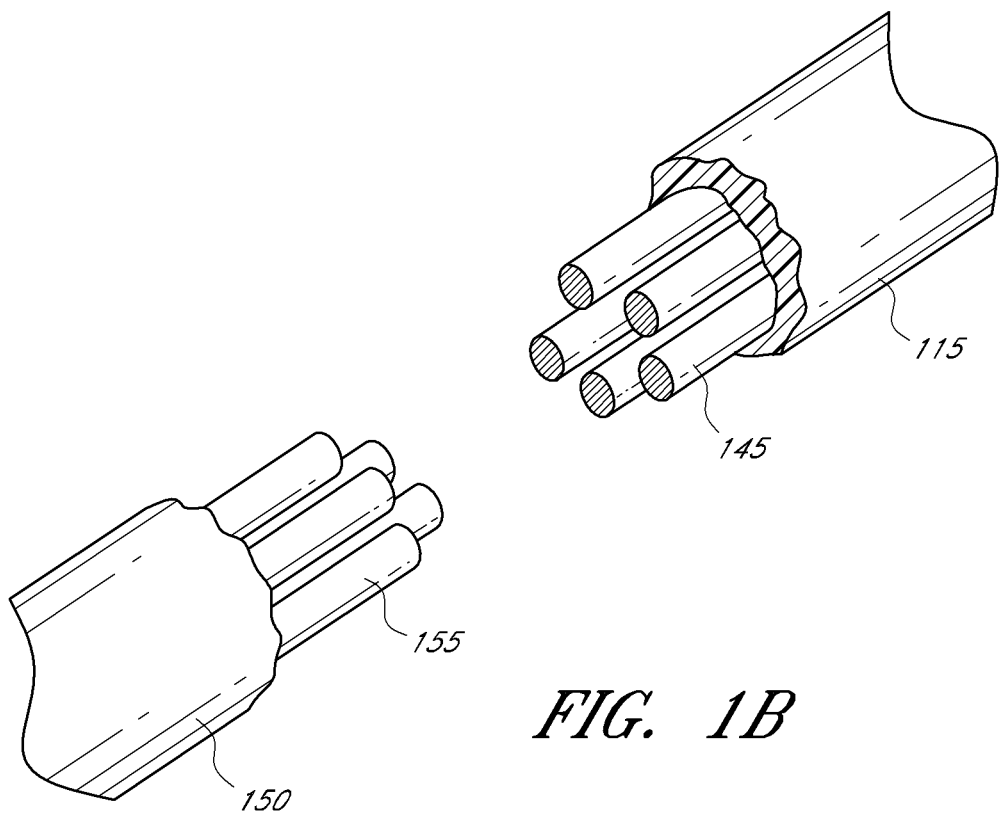
FIGS. 1B and 1C illustrate the attachment of a new sensor assembly to a reused sensor cable of FIG. 1A.
Figure 1C:
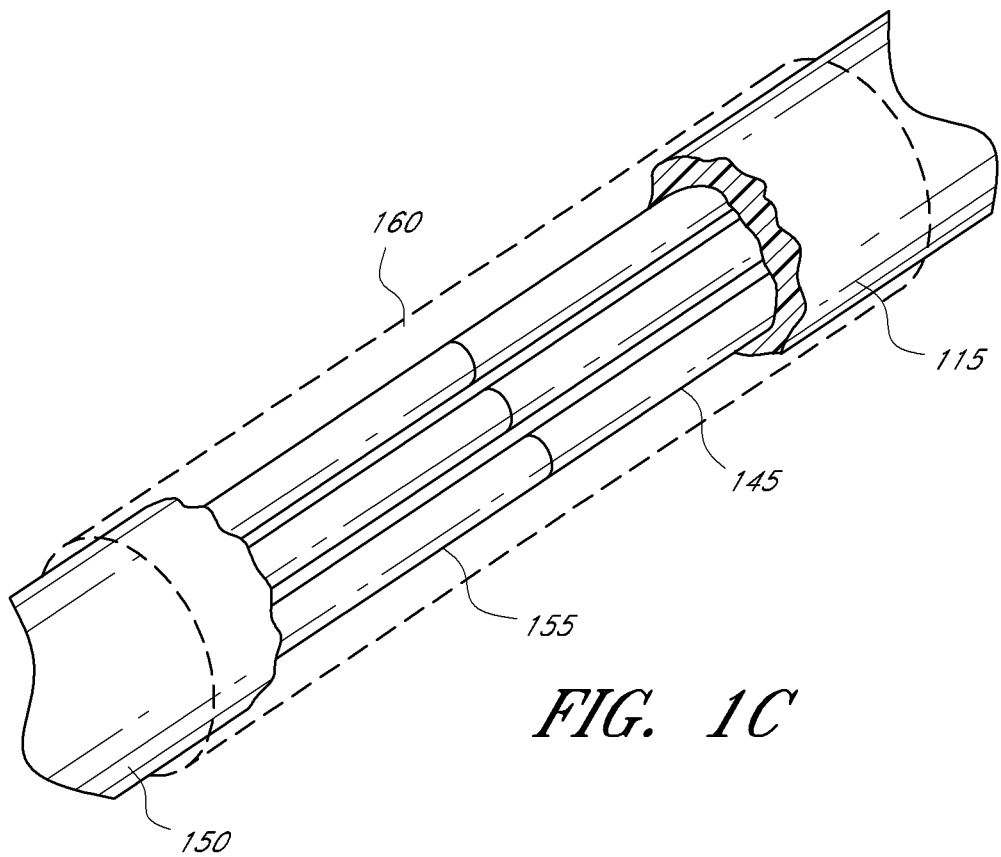

FIGS. 1B and 1C illustrate the attachment of a new sensor assembly to a reused sensor cable 115 of FIG. 1A. The sensor cable 115 having a number of wires 145 is attached to a new sensor assembly having a number of wires 155. In one embodiment, the sensor assembly 150 includes a cable portion extending from the sensor assembly containing the sensor assembly wires 155. In one embodiment, at least part of the cable covering the wires 145, 155 is removed to expose the wires 145, 155 for easier access.

In FIG. 1C, the wires 145, 155 are attached to operatively connect the sensor cable 115 and the sensor assembly 150. The connection can be both mechanical and electrical. Attachment of the wires 145, 155 can be through soldering, pressure, tying, adhesive and/or the like. A cable covering 160 can be applied over the connection area to cover exposed wires and/or strengthen the mechanical connection between the cable 115 and the sensor assembly 150.

Although disclosed with reference to the above sensor 100, an artisan will recognize from the disclosure herein a wide variety of oximeter sensors, optical sensors, noninvasive sensors, medical sensors, disposable sensors, reusable sensors or the like that may benefit from embodiments of the refurbishing process disclosed herein.

Figure 2:
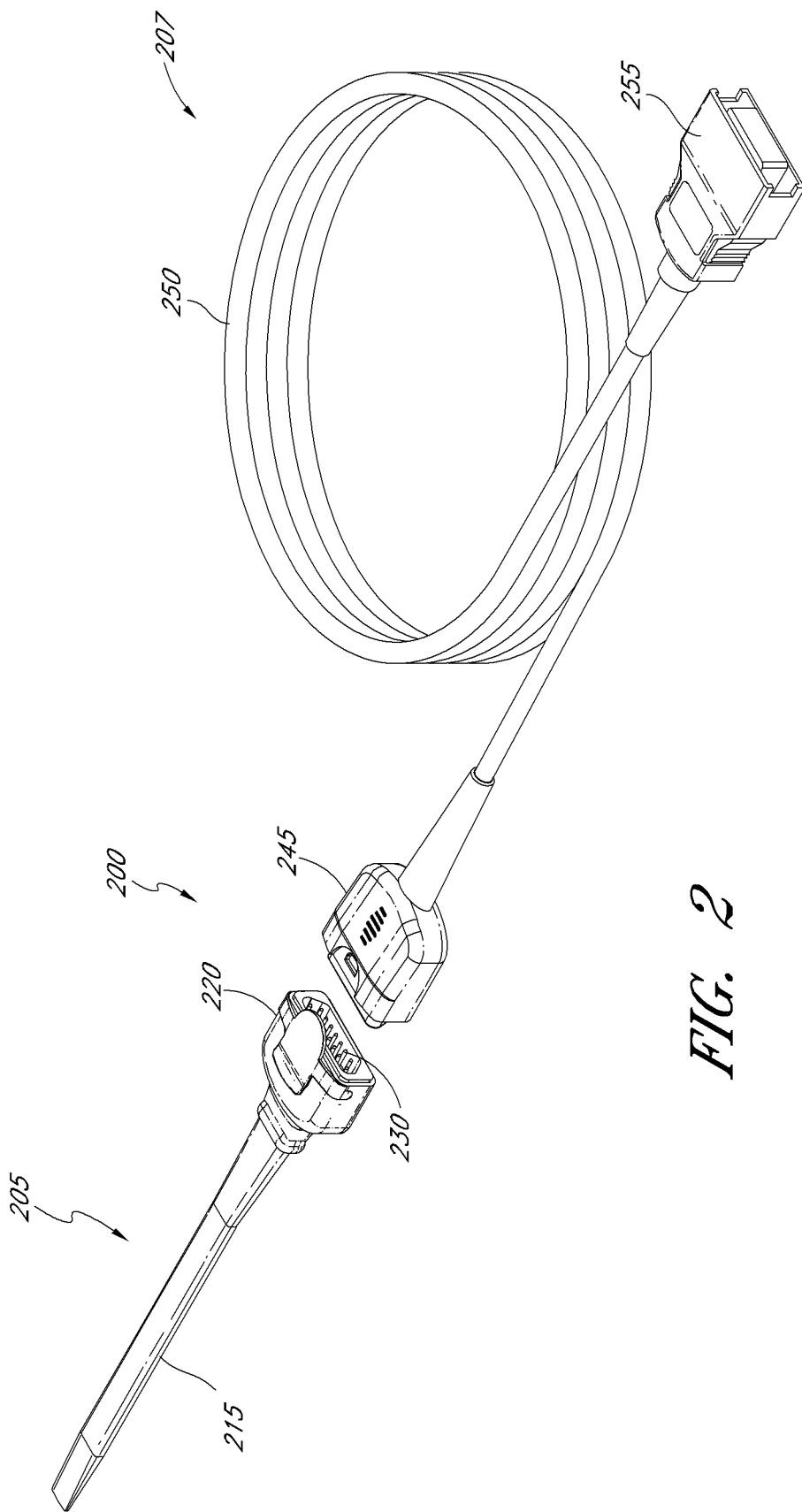
FIG. 2 illustrates a perspective view of a sensor embodiment having a detachable sensor assembly usable in a refurbishing process.

FIG. 2 illustrates a perspective view of a sensor embodiment 200 having a detachable sensor assembly 205 usable in a refurbishing process. The sensor 200 includes the sensor assembly 205 and a cable assembly 207. The sensor assembly 205 includes a sensor, a cable 215 and a connector 220. The cable assembly includes a connector 245, a cable 250 and a monitor connector 255. The sensor connector 220 is attachable to the cable connector 245. The connectors 220, 245 form a releasable mechanical and electrical connection between the sensor assembly and the cable assembly. The connectors 220, 245 can include pins 230 and corresponding pin connectors for forming an electrical connection between the sensor portion 205 and cable portion 207. Connector assemblies are disclosed in U.S. application Ser. No. 12/248,856 assigned to Masimo Corp. and is incorporated by reference herein.

During reprocessing, the connectors 220, 245 facilitate replacement of either the sensor assembly 205 or the cable assembly 207 of the sensor 200. For example, the sensor portion 205 can be replaced whole by detaching the old sensor assembly 205 from the cable assembly 207 via the sensor connector 220 and replacing with a new sensor assembly by attaching the new sensor connector to the old cable connector 245. The use of a connector also allows replacement of the sensor assembly 205 on-site, for example at a hospital. The sensor assembly 205 can then be sent for refurbishing without also sending the cable assembly, thus reducing shipping costs.

Figure 3A:
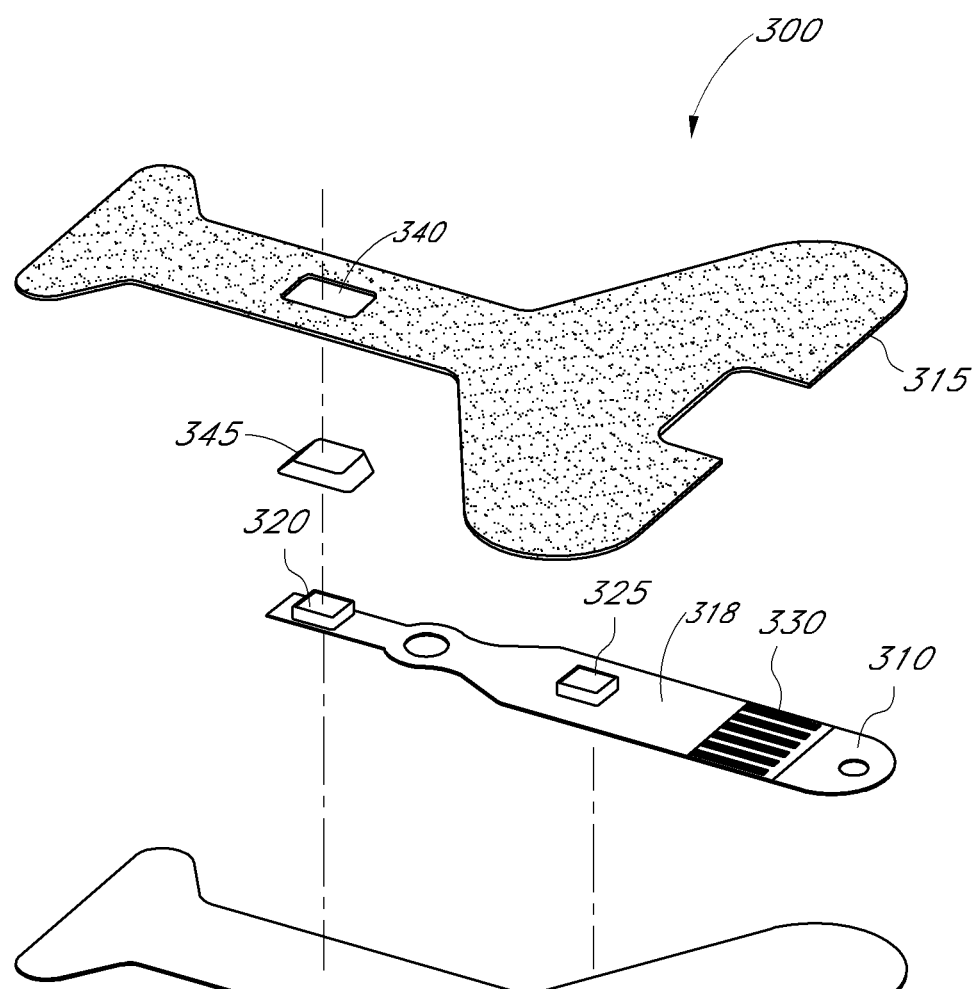
FIG. 3A illustrates an exploded perspective view of a disposable sensor assembly usable in a refurbishing process.

FIG. 3A illustrates an exploded perspective view of a disposable sensor assembly 300. The sensor assembly includes one or more tape layers 305, 315 and a sensor portion 310. The sensor portion 310 includes a base material 318, one or more sensing components 320, 325 such as emitters and/or detectors, and an electrical connector 330. The sensor portion can further include a sensor cover 345 for one or more of the sensing components. Sensor components can be replaced individually or together as part of the sensor portion 310.

In one embodiment, the base material 318, preferably a flexible material, comprises a flex circuit. The flex circuit can comprise a copper/MYLAR™ or copper/Capton™ laminant, or similar material. Alternatively, the flex circuit can be formed by depositing a conductive ink on MYLAR™, polyester, or plastic film. The flex circuit allows electrical communication between the sensing components 320, 325 and electrical connector 330 through the conductive material on the flex circuit.

The sensing components 320, 325 can be attached to the base material 318 through pressure sensitive adhesive (PSA), solder, clip holder, pressure fit or the like. In one embodiment, the emitter and detector are placed such that the transmission and detection field of view are through detector and emitter windows formed on the base material.

In one embodiment, the sensing components 320, 325 are attached to the flex-circuit using pressure or thermally sensitive adhesive configured to provide a temporary bond, advantageously allowing the sensing components 320, 325 to be detached from the sensor portion 310 by pulling the sensing components from the base material 318. As will be apparent, other attachment methods can be used that facilitate removal of sensor components in order to simplify the refurbishing process, such as nodular metal paste, mechanical attachments, or the like.

In another embodiment, the sensing components are attached to the flex-circuit using low temperature solder paste. The sensing components can be desoldered from the flex circuit. The solder can be reheated and reused or new solder can be dispensed on contacts for the detector connections and/or emitter connections in order to attach new sensing components. The solder operation is preferably performed through a direct heat reflow of the low temperature solder.

The sensor portion 310 can further comprise a flex circuit shield including an insulator film, conductive and/or non-conductive PSA. When attached to a flex circuit, a flex circuit shield can insulate the signal traces of the flex circuit from the metallization of the flex circuit shield to prevent short circuits. The sensor portion 310 can be attached to a base layer 305. In one embodiment, the base layer comprises Avery base material. Each side of the base layer can be coated with PSA adhesive.

A face stock 315 can be attached to the base layer 305 such that the sensor portion 310 is secured between the face stock and the base material. In one embodiment, the face stock 315 is advantageously constructed from a non-woven, flexible material, though woven materials can be used. Adhesive can be applied on one side of the face stock. Pressure applied to the face stock 315 bonds the face stock with the base material 305 and/or sensor portion 310. Preferably, the face stock has an aperture 340 to allow a portion of the cover 345 to protrude through the face stock. A release liner can be placed on the other side of the base material from the face stock in order to protect adhesive on that side. The release liner can be removed when the sensor is attached to a patient.

During reprocessing, the sensor assembly 300 can be disassembled into its constituent parts. For example, the face stock 315 can be detached from the base material 305 to expose the sensor portion 310. The sensing components 320, 325 on the sensor portion can be replaced individually or together as part of the sensor portion 310. In one embodiment, the sensing components 320, 325 are replaced individually with at least some of the sensor portion 310 retained. After replacing the sensing components, the sensor can be reassembled. The base layer 305, face stock 315, and/or cover 345 can be replaced or reused. New adhesive can be applied to the sensor assembly 300 and a release liner attached. Once reassembled, the sensor assembly 300 can be sterilized and then packaged for use.

Figure 3B:
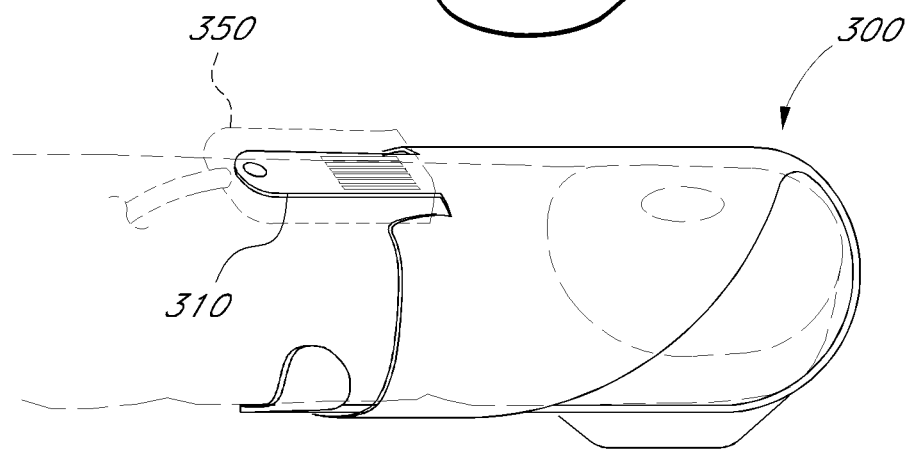
FIG. 3B illustrates the disposable sensor of FIG. 3A attached to a tissue site and a cable assembly

FIG. 3B illustrates the disposable sensor of FIG. 3A attached to a tissue site and a cable assembly. The cable assembly 350 comprises a cable and a connector attachable to the sensor assembly 300 via its sensor connector 330. The cable assembly 350 operatively connects the sensor assembly 300 to a patient monitor. The cable portion 350 can also be reprocessed with the sensor assembly 300 and replaced if defective. However, as the cable portion generally receives less wear than the sensor assembly 300, the cable portion can likely be reused without replacement of components, reducing the cost of reprocessing the sensor.

Figure 4:
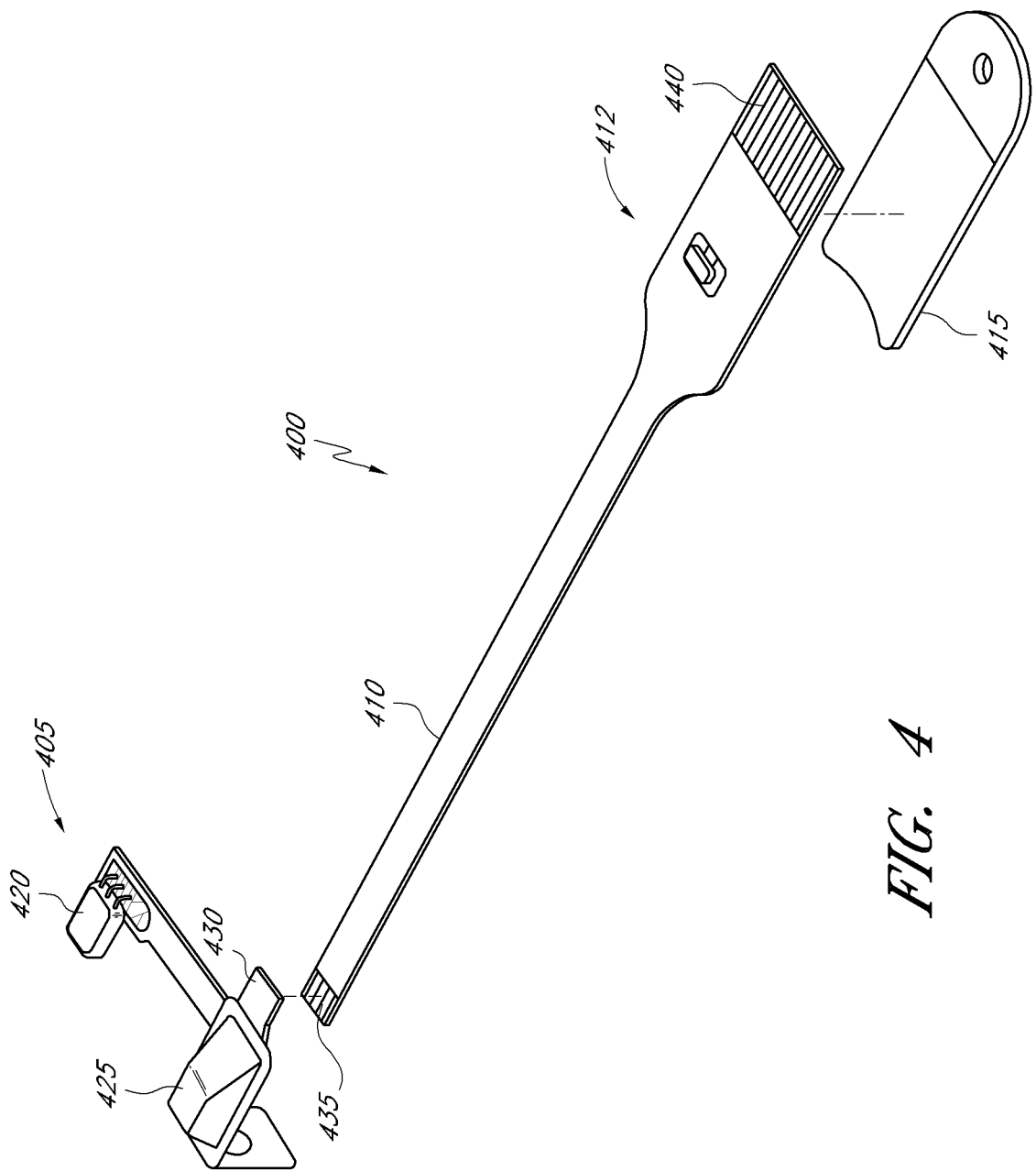
FIG. 4 illustrates a perspective view of a neonate sensor assembly with a detachable sensor portion usable in a refurbishing process.

FIG. 4 illustrates a perspective view of a neonate sensor assembly 400 with a detachable sensor portion 405 usable in a refurbishing process. The sensor includes the sensor portion 405, an elongated body 410, and a connector portion 412. The sensor portion 405 incorporates one or more emitters 420, a detector assembly 425, and a sensor portion pinout 435. The sensor portion pinout 430 is configured to connect with a body pinout 430 so as to mechanically and electrically connect the sensor to the body 410. Connection can be accomplished by solder, adhesive, mechanically such as by tab, sleeve or clip, or by other connection mechanism. The body 410 includes signal traces between the sensor portion pinout 435 and the connector portion 412. The connector portion 412 has a plug portion configured to insert into a mating patient cable connector so as to mechanically and electrically connect the sensor 400 to a patient cable, for example. The connector portion 412 is configured with a connector tab 415 supporting sensor pinouts 440.

As the sensor portion 405 is detachable from the elongate body 410, reprocessing of the sensor is simplified. For example, the sensor portion 405 can be detached from the elongate body and replaced with a new sensor portion 405. By incorporating sensing elements, such as the emitters 420 and the detector 410 on the detachable modular portion, the sensing elements can be easily replaced as a whole rather than individually, thus reducing refurbishing costs and refurbishing time. In one embodiment, the sensing elements can be pre-tested in order to eliminate or reduce the need for testing the sensor elements.

Figure 6:
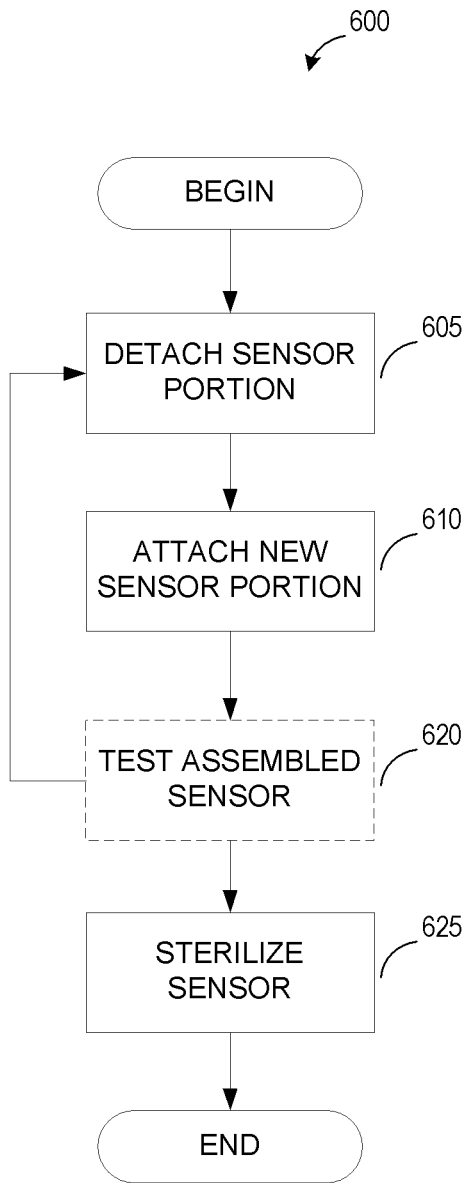
FIG. 6 illustrates another embodiment of a refurbishing process for sensors comprising replaceable modular assemblies.

FIGS. 5A, 5B and 6 illustrate flow charts for embodiments of a refurbishing process replacing sensor components. The refurbishing process can be used for the sensors described in FIGS. 1A-4 and FIGS. 7-9B, as well as other types of sensors. In some embodiments, the refurbishing process may be performed by a computing system comprising one or more computing devices, the one or more computing devices configured to perform one or more of the logical blocks described below. The logical blocks of the refurbishing process can be embodied as software, hardware, or a combination of software and hardware of the computing system. For example, the refurbishing process may be embodied in software stored on non-transitory, physical computer storage such as a hard drive, optical disk or flash memory. In some embodiments, the computing system may be part of a refurbishing system comprising one or more machines configured to dissemble sensors, replace sensor components, test sensors and/or sterilize sensors. In one embodiment, the computing system directs or monitors the operation of the refurbishing machines. In one embodiment, the machines operate automatically. In some embodiments, one or more logical blocks may be performed by or directed by a person. For example, the entire refurbishing process may be performed by or directed by one or more persons.

In FIG. 5A the process 500 begins at block 505 with disassembling the sensor, in whole or in part, into subcomponents or individual components. Sensors can be disassembled through desoldering, removing adhesive, detaching connectors, or the like.

At bock 510, the sensor components can optionally be tested. For example, sensor components can be tested to determine if performance is within specification. Sensor components within specification can be reused. Testing of components can be skipped to reduce cost and/or speed up the refurbishing process.

In one embodiment, testing can be conducted before disassembly to determine if the sensor as a whole is within specification. Generally, sensors need to meet specified sensor performance criteria determined by the manufacturer or purchaser. By testing before disassembly, out-of-specification sensing components can be detected beforehand and the sensing portion can be replaced as a whole without disassembly. In contrast, by testing after disassembly, a specific out-of-spec component can be identified, allowing reuse of the other parts of the sensing portion that are still in-spec. The timing of the testing can be chosen based on the costs of disassembly versus the savings from reusing still in-specification components. After block 510, the refurbishing process proceeds to block 515.

At block 515, sensor components are replaced. In one embodiment, sensor components are replaced if determined to be out-of-spec. In another embodiment, no testing is performed and pre-determined sensor components are replaced. For example, as part of the refurbishing process, all or some of the sensing components can be replaced without testing. Advantageously, predetermined replacement of components can eliminate or reduce the need for testing or disassembly. After block 515, the refurbishing process proceeds to block 520.

At block 520, the sensor is reassembled. Reassembly can comprise soldering, adhesively connecting, and/or mechanically connecting various components together. Typically, the assembled sensor comprises both new components and at least some of the original components. After block 520, the refurbishing process proceeds to block 525.

At block 525, the assembled sensor is optionally tested to determine if the sensor works and is within specification for the particular sensor type. Testing can include testing of the assembly of the sensor components, testing of the electrical connection between sensor components, testing of sensor performance, and/or the like. If the test fails, the sensor can reenter the refurbishing process at block 505 or can be disposed of. If the sensor passes the test, the refurbishing process proceeds to block 530. In some embodiments, testing may be unnecessary during reprocessing, such as when the sensor components are pre-tested before assembling the sensor.

At block 530, the sensor is sterilized. Sterilization can occur before or after the sensor is packaged for use. The sensor can also be cleaned before sterilization. After sterilization, the sensor can be packaged for use, ending the refurbishing process.

FIG. 5B generally illustrates the same process as FIG. 5A, except that optional block 510, testing of the sensor components, occurs before block 505, disassembling the sensor. Testing of the components can be individually, by group, or of the whole sensor. By testing the sensor components before dissembling the sensor, components that need to be replaced can be identified before disassembly, potentially reducing the number of components to be detached.

FIG. 6 illustrates another embodiment of a refurbishing process 600 for a sensor comprising replaceable modular assemblies. The refurbishing process can be used for the sensors described in FIGS. 1A-4 and FIGS. 7-9B, as well as other types of sensors. In one embodiment, the sensor is composed of modules, such as a sensor assembly and a cable assembly. In some embodiments, a sensor assembly comprises a modular sensor portion. The sensor portion can further comprise adhesive portions, a sensor body, and/or electrical or mechanical connectors. During reprocessing, the modular assembly is replaced. By replacing the modular assembly as a whole, the need for testing sensor components can be reduced or eliminated, thus reducing costs. For example, in FIG. 1A, the sensor assembly 100 can be replaced as whole. Likewise with the sensor assembly 205 of FIG. 2, the sensor portion 310 of FIG. 3, and the sensor portion 405 of FIG. 4. Furthermore, modular assemblies can be pre-tested during their production, simplifying the refurbishing process.

At block 605, the refurbishing process begins by detaching the modular assembly from the sensor. In some embodiments, a sensor portion 405 (in FIG. 4) is detached from a sensor assembly 400. In some embodiments, a sensor assembly 105 (in FIG. 1) is detached from a cable assembly 140, for example, by cutting the sensor assembly from the cable. In some embodiments, detaching of the modular assembly can be simplified by using a connector 220 (in FIG. 2), 405 (in FIG. 4). After block 605, the refurbishing process proceeds to block 610.

At block 610, the modular assembly is attached to the sensor. The attached modular assembly can be a sensor portion attached to a sensor assembly or a sensor assembly attached to a cable assembly. Typically, the assembled sensor comprises both new components and at least some of the original components. Generally, the cable assembly receives less wear and tear during use and is likely to perform within specification without replacement. However, in some situations, the cable assembly can be replaced in addition or instead of the sensor portion or assembly. Reattachment can be accomplished through use of a connecter, splicing of wires, adhesive connection, soldering, or the like.

As replacement is accomplished by replacing groups of components, such as a sensor assembly, cable assembly, and/or a sensor portion, reassembly of the sensor is simplified in comparison to replacement of individual components. If component costs are cheap relative to assembly and disassembly cost, the simplified reassembly can reduce the costs of refurbishing. After block 610, the refurbishing process proceeds to block 620.

At block 620, the assembled sensor is optionally tested to determine if the sensor works and is within specification for the particular sensor type. Testing can include testing of the assembly of the sensor components, testing of the electrical connection between sensor components, testing of sensor performance, and/or the like. If the test fails, the sensor can reenter the refurbishing process at block 605 or can be disposed of. If the sensor passes the test, the refurbishing process proceeds to block 625. In some embodiments, testing during reprocessing may be unnecessary, such as when the sensor portion is pre-tested before assembling the sensor.

At block 625, the sensor is sterilized. Sterilization can occur before or after the sensor is packaged for use. The sensor can also be cleaned before sterilization. Once packaged, the sensor can be delivered to an end-user.

Figure 7:
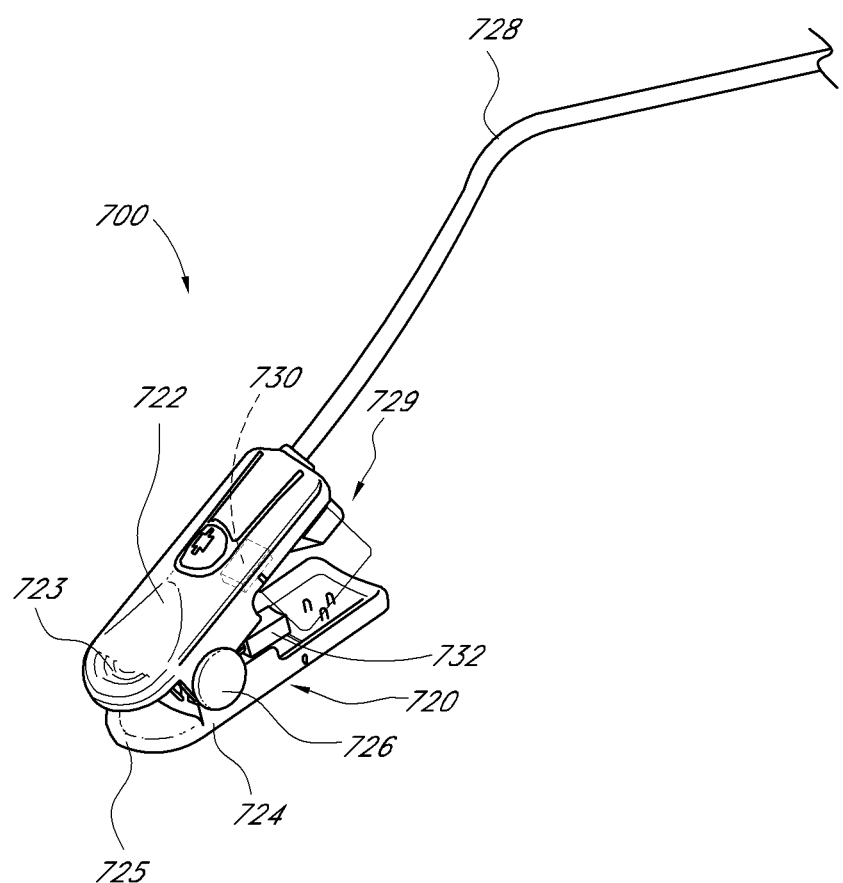
FIG. 7 illustrates a perspective view of one embodiment of reusable sensor usable in a refurbishing process according to embodiments of the disclosure.

FIG. 7 illustrates a perspective view of one embodiment of reusable sensor 700 usable in a refurbishing process according to embodiments of the disclosure. The reusable sensor can be a clip-type sensor including an upper housing 722, a lower housing 724 and a hinge element 726. The upper and lower housings 722, 724 house electrical and/or optical components (not shown) of the non-invasive physiological sensor 720. For example, the upper and lower housings 722, 724 can house sensing elements 730, 732, such as one or more light emitters or LEDs and a detector or light sensor. The sensor 720 can be connected to a patient monitor via a cable 728. For example, the detector outputs a signal to the monitor over the cable 728 which then processes the signal to provide a numerical readout of physiological parameters such as oxygen saturation (SpO2) and pulse rate.

Figure 8A:
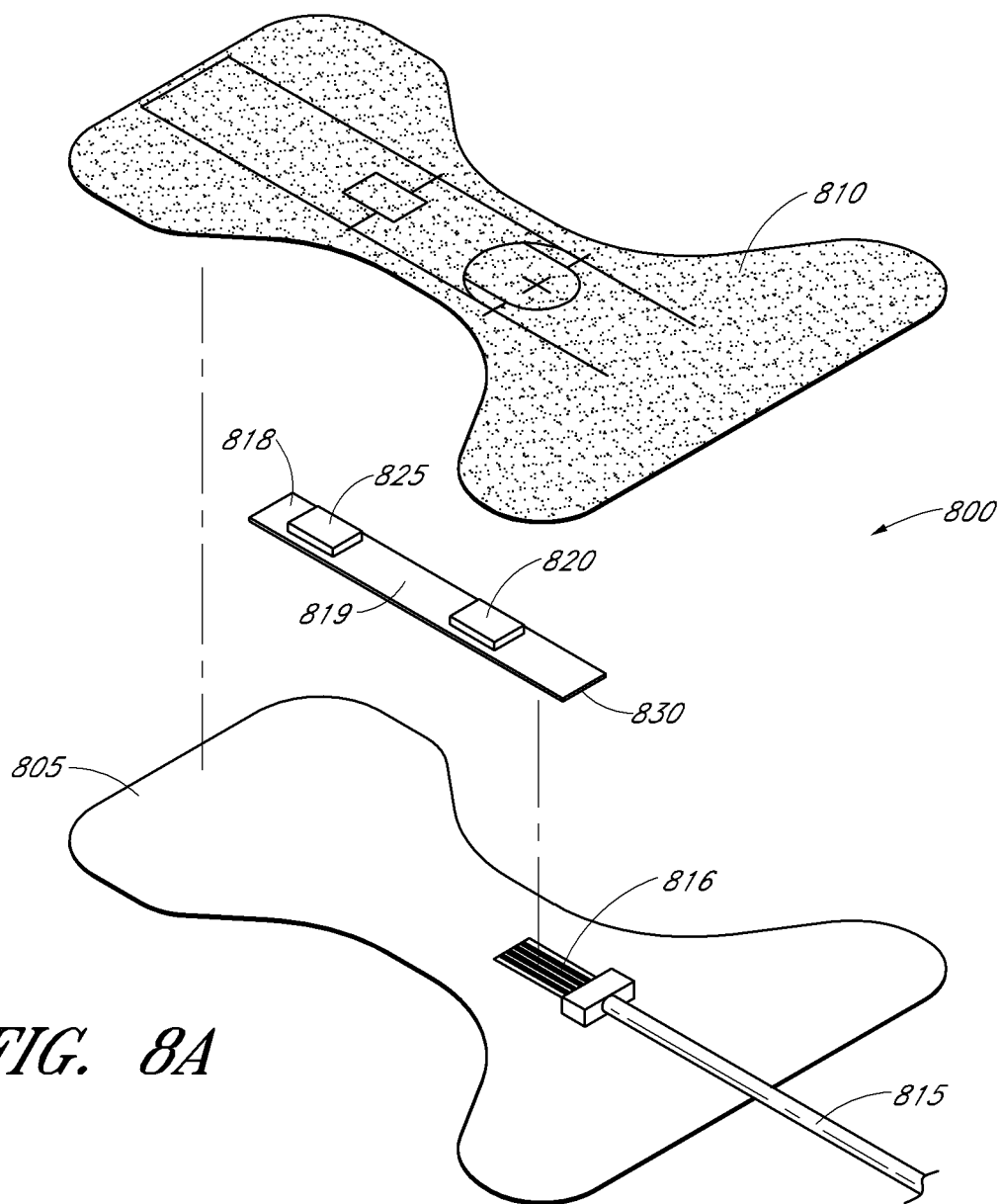
FIG. 8A illustrates an exploded perspective view of an embodiment of a disposable sensor 800 usable in a refurbishing process according to embodiments of the disclosure.

During refurbishing, one or both the sensing elements 730, 732 can be removed and/or replaced from the reusable sensor 700. The sensor elements can be tested separately or as part of the reusable sensor. Other components of the reusable sensor can also be replaced during the refurbishing process, FIG. 8A illustrates an exploded perspective view of an embodiment of a disposable sensor 800 usable in a refurbishing process according to embodiments of the disclosure. The sensor includes one or more tape layers 805, 810, a cable assembly 815, and a sensor portion 818. The cable assembly 815 can terminate at an electric connector 816 and can be attached to one of the tape layers 805. The sensor portion 818 includes a base material 819, one or more sensing components 820, 825 such as emitters and/or detectors, and an electrical connector 830. Sensor components can be replaced individually or together as part of the sensor portion 818. The sensor portion's electrical connector 830 can attach to the cable assembly's electrical connector 816 to form an electrical connection between the sensor portion and the cable. The sensor portion 818 can be attached to the cable assembly 815 and/or one or more tape layers 805, 810 by various ways, such as adhesive, solder, clip holder, pressure fit and/or the like. In one embodiment, the sensor assembly 815 and sensor portion 818 are sandwiched between a first layer 805 and a second 810 tape layer.

As the sensor portion 818 is detachable from the cable assembly 815 and/or tape layers 805, 810, reprocessing of the sensor is simplified. For example, the sensor portion 818 can be detached from the elongate body and replaced with a new sensor portion. By incorporating sensing components 820, 825, such as emitters and/or detectors on the detachable modular portion, the sensing components can be easily replaced as a whole rather than individually, thus reducing refurbishing costs and refurbishing time. In one embodiment, the sensing components can be pre-tested in order to eliminate or reduce the need for testing the sensing components during the refurbishing process.

Figure 8B:
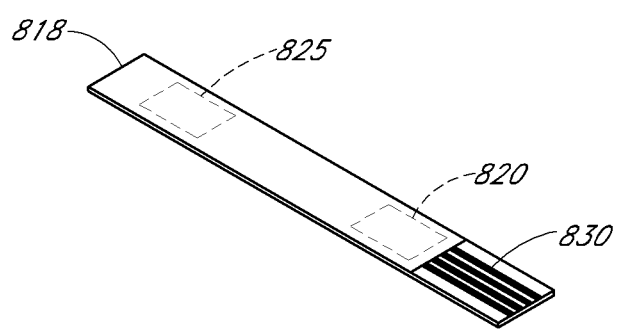
FIG. 8B illustrates a perspective view of the bottom side of the sensor portion of FIG. 8A.

FIG. 8B illustrates a perspective view of the bottom side of the sensor portion 818 of FIG. 8A. The electrical connector 830 is shown on the bottom side of the sensor portion. However, the electrical connector can also be placed on the top side.

FIGS. 9A and 9B illustrate embodiments of mechanical sensor component holders. FIG. 9A illustrates a cross-sectional view of a sensor component attached to a sensor via a clip holder. The sensor component 905 is held in place by one or more clip arms 910 extending over the sensor component. The sensor component 905 can be detached for replacement by pushing the clip arms 910 outward and removing the sensor component 905.

FIG. 9B illustrates a cross-sectional view of a sensor component attached to a sensor via a pressure or snug fit holder. The sides of the holder 915 are biased inwards, holding the sensor component together via pressure. The sensor component 905 can be detached for replacement by pushing the sides of the holder 915 outward and removing the sensor component 905.

The reusable nature of the mechanical holders allows replacement of the sensor component without requiring new attachment mechanisms, such as replacement adhesive or solder, thus reducing refurbishing costs and/or complexity. As will be apparent, other types of mechanical holders can be used and mechanical holders can be used with both disposable and reusable sensors.

Depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal. Data may be stored in various types of data stores, such as tables, files, databases, directories or the like.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. Also, the term "or" is used in its inclusive sense (and not in its exclusive sense) so that when used, for example, to connect a list of elements, the term "or" means one, some, or all of the elements in the list.

Various reprocessing and refurbishing processes have been disclosed in detail in connection with various embodiments. These embodiments are disclosed by way of examples only and are not to limit the scope of the claims that follow. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein. One of ordinary skill in the art will appreciate the many variations, modifications and combinations. For example, the various embodiments of the reprocessing and refurbishing process can be used with sensors that can measure any type of physiological parameter and with both disposable and reusable sensors.

What is claimed is:

1. A reprocessed physiological sensor comprising:
a first electrical contact;
a first physiological sensor component coupled to the first electrical contact, wherein:
the first electrical contact is configured to communicate signals to and/or from the first physiological sensor component, and
the first physiological sensor component is not a replacement physiological sensor component;
a second electrical contact;
a second physiological sensor component coupled to the second electrical contact, wherein:
the second electrical contact is configured to communicate signals to and/or from the second physiological sensor component,
the second physiological sensor component is a replacement physiological sensor component for a previously used physiological sensor component, and
the second physiological sensor component is configured to operate within a specification of the reprocessed physiological sensor; and
a used cable assembly that has been detached from a used physiological sensor and newly attached to the first and second electrical contacts, wherein the used cable assembly has been detached from the used physiological sensor by cutting a plurality of wires, and wherein the used cable assembly has been attached to the first and second electrical contacts by connecting corresponding ones of the previously cut plurality of wires.

2. The reprocessed physiological sensor of claim 1, wherein the second physiological sensor component was newly coupled to the second electrical contact when the second physiological sensor component replaced the previously used physiological sensor component that was uncoupled from the second electrical contact.

3. The reprocessed physiological sensor of claim 1, wherein the used cable assembly comprises a first end including a monitor connector and a second end from which the used physiological sensor was detached.

4. The reprocessed physiological sensor of claim 3 further comprising:
a cable cover covering at least a portion of the used cable assembly where the used cable assembly is newly attached to the first and second electrical contacts, wherein the cable cover covers exposed wires and/or strengthens a mechanical connection between the used cable assembly and the first and second electrical contacts.

5. The reprocessed physiological sensor of claim 4, wherein a performance of the previously used physiological sensor component has been determined to not satisfy a threshold.

6. The reprocessed physiological sensor of claim 5, wherein a performance of the second physiological sensor component has been determined to satisfy the threshold.

7. The reprocessed physiological sensor of claim 6, wherein the second physiological sensor component includes at least one of an emitter or a detector.

8. The reprocessed physiological sensor of claim 7, wherein the reprocessed physiological sensor is a pulse oximetry sensor.

9. The reprocessed physiological sensor of claim 8, wherein the used cable assembly has been sterilized.

10. A reprocessed physiological sensor comprising:
a first physiological sensor component that is not a replacement physiological sensor component and which comprises a first electrical contact;
a second physiological sensor component that is a replacement physiological sensor component for a previously used physiological sensor component and which comprises a second electrical contact; and
a used cable assembly that has been detached from a used physiological sensor and newly made a part of the reprocessed physiological sensor so as to communicate signals to and/or from the first and second physiological sensor components, wherein the used cable assembly has been detached from the used physiological sensor by cutting a plurality of wires, and wherein the used cable assembly is made a part of the reprocessed physiological sensor via connecting corresponding ones of the previously cut plurality of wires to the first and second electrical contacts.

11. The reprocessed physiological sensor of claim 10, wherein:
a performance of the previously used physiological sensor component has been determined to not satisfy a threshold, and
a performance of the second physiological sensor component has been determined to satisfy the threshold.

12. The reprocessed physiological sensor of claim 11, wherein:
the reprocessed physiological sensor is a pulse oximetry sensor, and
the second physiological sensor component includes at least one of an emitter or a detector.

13. The reprocessed physiological sensor of claim 12 further comprising:
a cable cover covering at least a portion of the used cable assembly where the used cable assembly is newly connected to the first and second electrical contacts, wherein the cable cover covers exposed wires and/or strengthens a mechanical connection between the used cable assembly and the first and second electrical contacts.

14. A method for reprocessing a previously used physiological sensor, the sensor including a plurality of physiological sensor components and a cable component, the method comprising:
determining a physiological sensor component of the plurality of physiological sensor components is to be replaced, wherein the physiological sensor component to be replaced does not comprise all of the plurality of physiological sensor components or the entire physiological sensor;
detaching the physiological sensor component to be replaced from the cable component, wherein detaching the physiological sensor component to be replaced from the cable component comprises cutting a wire;
obtaining a replacement physiological sensor component that operates within a specification of the physiological sensor and which comprises an electrical contact; and
attaching the replacement physiological sensor component to the cable component to form a reprocessed physiological sensor, wherein attaching the replacement physiological sensor component to the cable component comprises connecting the previously cut wire to the electrical contact.

15. The method of claim 14 further comprising:
providing a cable cover covering at least a portion of the cable component where the cable component is attached to the replacement physiological sensor component, wherein the cable cover covers exposed wires and/or strengthens a mechanical connection between the cable component and the replacement physiological sensor component.

16. A method for reprocessing a previously used physiological sensor, the sensor including a plurality of physiological sensor components, the method comprising:
determining a physiological sensor component of the plurality of physiological sensor components is to be replaced, wherein the physiological sensor component to be replaced does not comprise all of the plurality of physiological sensor components or the entire physiological sensor;
detaching the physiological sensor component to be replaced from a first electrical contact of the physiological sensor;
obtaining a replacement physiological sensor component that operates within a specification of the physiological sensor, wherein a second electrical contact extends from the replacement physiological sensor component;
attaching the second electrical contact extending from the replacement physiological sensor component to the first electrical contact to form a reprocessed physiological sensor; and
attaching a used cable assembly that has been detached from a used physiological sensor to a portion of the previously used physiological sensor so as to communicate signals to and/or from the replacement physiological sensor component, wherein detaching used cable assembly from the used physiological sensor component comprises cutting a wire, and wherein attaching the used cable assembly to the portion of the previously used physiological sensor comprises connecting the previously cut wire.

17. The method of claim 16 further comprising:
providing a cable cover covering at least a portion of the used cable assembly where the used cable assembly is attached to the re used physiological sensor, wherein the cable cover covers exposed wires and/or strengthens a mechanical connection between the used cable assembly and the used physiological sensor.

* * * * *